United States Patent [19]

Ohba et al.

[11] 4,242,327

[45] Dec. 30, 1980

[54] ANTIBIOTIC SF-2052 SUBSTANCE AND PRODUCTION AND USE THEREOF

[75] Inventors: Kazunori Ohba; Takashi Shomura, both of Yokohama; Michio Kojima; Shoji Omoto, both of Tokyo; Takashi Tsuruoka, Kawasaki; Shigeharu Inoue, Yokohama, all of Japan

[73] Assignee: Meiji Seika Kaisha, Ltd., Tokyo, Japan

[21] Appl. No.: 89,924

[22] Filed: Oct. 31, 1979

[30] Foreign Application Priority Data

Nov. 6, 1978 [JP] Japan .................................. 53-135921

[51] Int. Cl.³ .............................................. A61K 35/00
[52] U.S. Cl. .................................... 424/116; 435/169; 536/17 R
[58] Field of Search .................... 424/116; 536/17; 435/169

[56] References Cited

U.S. PATENT DOCUMENTS 3,976,768  8/1976  Nara et al. ........................... 424/118

*Primary Examiner*—Jerome D. Goldberg
*Attorney, Agent, or Firm*—Larson, Taylor and Hinds

[57] ABSTRACT

New antibiotic, SF-2052 substance is produced by cultivating a microorganism, *Dactylosporangium matsuzakiense* SF-2052 now deposited under FERM-P 4670 or ATCC No. 31570 in a liquid culture medium under aerobic conditions, and this antibiotic may be isolated from the culture broth by conventional method and is useful as antibacterial agent.

6 Claims, 3 Drawing Figures

ANTIBIOTIC SF-2052 SUBSTANCE AND PRODUCTION AND USE THEREOF

SUMMARY OF THE INVENTION

This invention relates to a new and useful antibiotic designated as SF-2052 substance. This invention also relates to the production of this new antibiotic by cultivating a strain of actinomycetes, particularly a strain of the genus Dactylosporangium in a culture medium. This invention further relates to an antibacterial composition comprising the SF-2052 substance as the active ingredient.

BACKGROUND OF THE INVENTION

A number of useful antibiotics are produced and isolated from the culture broth of various strains of microorganisms. In an attempt to discover new and useful antibiotics active against gram-negative and gram-positive bacteria as well as various bacteria strains resistant to the known antibiotics, we have made research on the fermentation broth of a new microorganism now designated as *Dactylosporangium matsuzakiense* SF-2052. As a result, we have now found that a new antibiotic is produced by cultivating this new microorganism in a culture medium containing assimilable nutrients under aerobic conditions. We have succeeded to isolate this new antibiotic from the culture broth and we have designated it as SF-2052 substance. We have determined chemical, physical and biochemical properties of SF-2052 substance.

An object of this invention is to provide a new antibiotic, SF-2052 substance which is useful as antibacterial agent. A further object of this invention is to provide processes of producing this new antibiotic using a strain of actinomycetes. Another objects will be clear from the following descriptions.

DETAILED DESCRIPTION OF THE INVENTION

Figure 1:
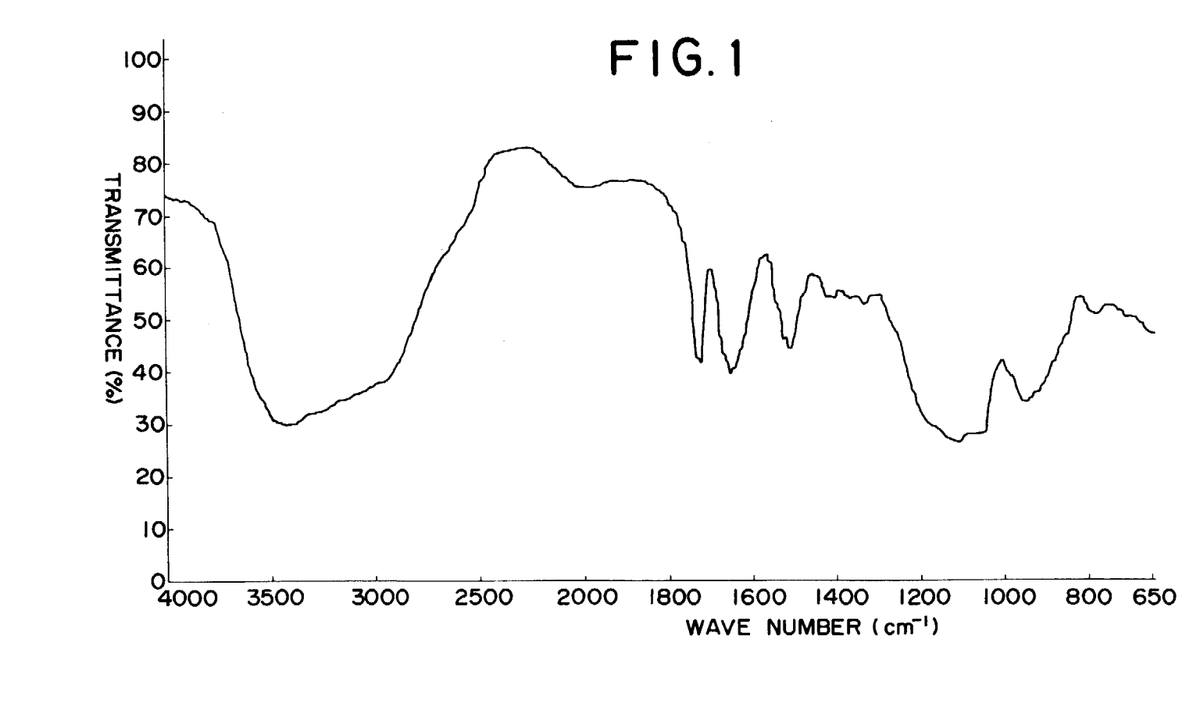
FIG. 1 shows a curve of the infrared absorption spectrum of a sample of the SF-2052 substance hydrochloride pelleted in potassium bromide.

According to this invention, there are firstly provided as a new antibiotic substance, SF-2052 substance and a pharmaceutically acceptable acid addition salt thereof, the SF-2052 substance being a water-soluble basic compound having antibacterial activity, and the SF-2052 substance hydrochloride being in the form of a colorless and amorphous powder which is substantially stable under neutral to acidic pH conditions but instable under alkaline pH conditions, which shows no definite melting point but discolors into brown gradually at or near 170° C. and is decomposed at 209°–210° C. with foaming, which shows positive reaction with ninhydrin, Lemieux reagent and Greig-Leiback's reagent but negative reaction with Sakaguchi's reagent and silver nitrate and which is readily soluble in water, soluble in methanol and insoluble in ethyl acetate, chloroform, benzene and ethylether;

the SF-2052 substance hydrochloride being further characterized by:

(a) exhibiting an elemental analysis: C 35.69%, H 7.04%, N 11.80%, (b) having no characteristic absorption peak at 220 nm to 370 nm in ultraviolet absorption spectrum in aqueous solution, (c) having an infrared absorption spectrum in potassium bromide pellet corresponding to that shown in FIG. 1 of the attached drawings, (d) having a hydrogen nuclear magnetic resonance absorption spectrum in deutero-water substantially corresponding to that shown in FIG. 2 of the attached drawings, (e) having a carbon nuclear magnetic resonance absorption spectrum in deutero-water substantially corresponding to that shown in FIG. 3 of the attached drawings, (f) having a specific optical rotation $[\alpha]_D^{25} = +87°$ (c=1, water) in aqueous solution, and (g) giving a single spot at Rf=0.46 in a cellulose thin layer chromatography with n-propanol-pyridine-acetic acid-water (15:10:3:12) as the developing solvent and at Rf=0.09 in a paper chromatography with n-butanol-acetic acid-water (2:1:1) as the developing solvent according to the ascending method.

The SF-2052 substance of this invention may be, for example, in the form of its acid-addition salt with a pharmaceutically acceptable inorganic acid such as hydrochloric acid, hydrobromic acid, sulfuric acid, nitric acid and phosphoric acid or with a pharmaceutically acceptable organic acid such as acetic acid, citric acid, benzoic acid, ascorbic acid or malic acid.

Propertes of the SF-2052 substance hydrochloride are summarized below.

1. Appearance: Colorless, amorphous powder
2. Melting point:
   No definite melting point. Slow discoloration into brown occurs by heating at or near 170° C., followed by decomposition at 209°–210° C. with foaming.
3. Elemental analysis:
   C 35.69%, H 7.04%, N 11.80%
4. Ultraviolet absorption spectrum:
   No characteristic absorption peak is observed at wave length ranging from 220 nm to 370 nm.
5. Infrared absorption spectrum:
   SF-2052 substance hydrochloride pelleted in potassium bromide gives an IR. spectrum shown in FIG. 1 of the attached drawings. Main absorption peaks observed at 2900–3500, 1720, 1640, 1510, 1120 and 1050 cm$^{-1}$.
6. Molecular weight:
   As SF-2052 substance is instable under alkaline pH conditions, its free base could not be obtained in a stable form, and it was very difficult to perform direct determination of molecular weight according to mass spectrometry. From carbon nuclear magnetic resonance spectrum and other some data available, it is estimated that SF-2052 substance (free base) has a molecular weight of approximately 400 to 450.
7. Solubility:
   Easily soluble in water, soluble in methanol and substantially insoluble in such organic solvents as chloroform, ethyl acetate, hexane, benzene and ethylether etc.
8. Stability:
   Relatively stable under acidic to neutral pH conditions but instable under alkaline pH conditions.
9. Rf values in cellulose thin layer chromatography:
   (a) Rf=0.46 when developed with n-propanol-pyridine-acetic acid-water (15:10:3:12 by volume)
   (b) Rf=0.10 when developed with n-butanol-acetic acid-water (2:1:1 by volume)
10. Rf values in paper chromatography (by ascending method):

(a) Rf=0.40 when developed with n-propanol-pyridine-acetic acid-water (15:10:3:12 by volume)

(b) Rf=0.09 when developed with n-butanol-acetic acid-water (2:1:1 by volume)

Figure 2:
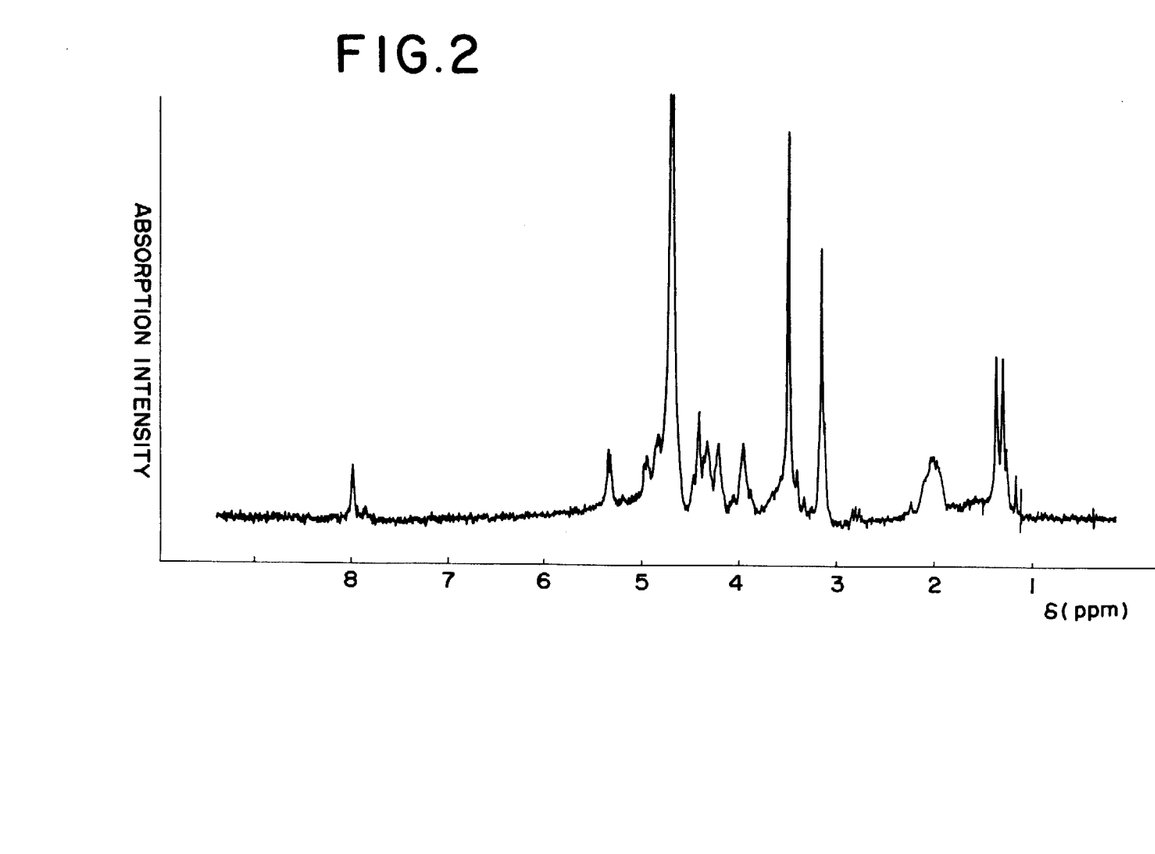
FIG. 2 shows a curve of the hydrogen nuclear magnetic resonance absorption spectrum of a sample of the SF-2052 substance hydrochloride in deutero-water at 100 MHz.
Figure 3:
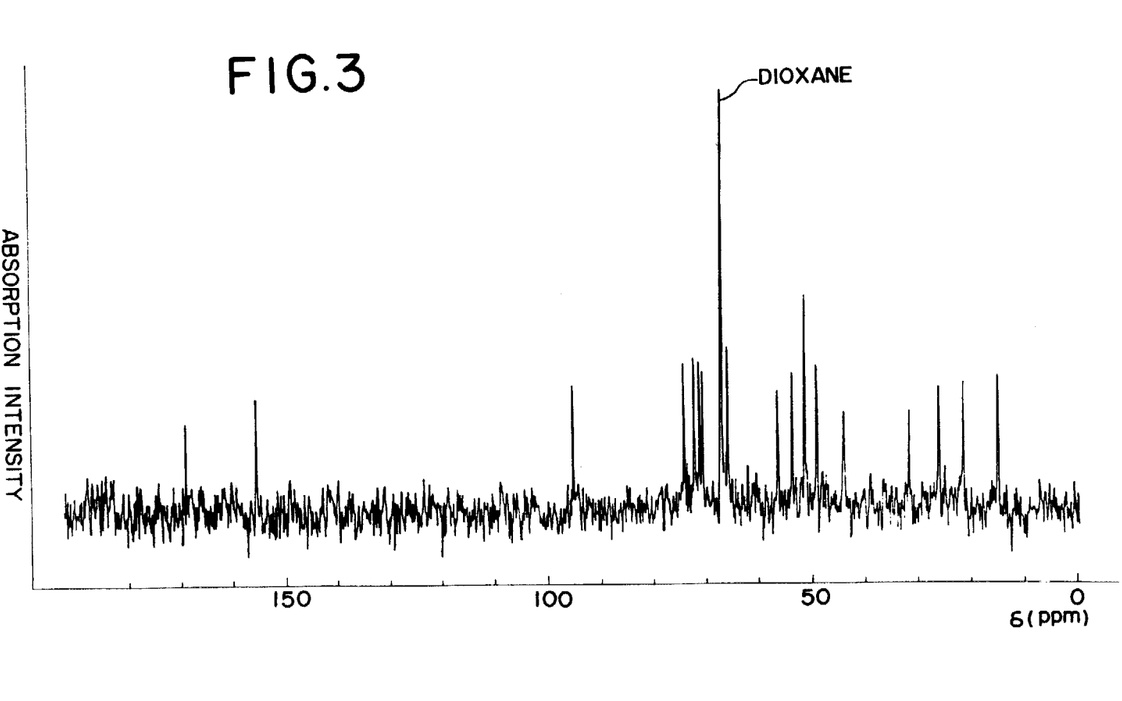
FIG. 3 shows a curve of the carbon nuclear magnetic resonance absorption spectrum of a sample of the SF-2052 substance hydrochloride in deutero-water at 25 MHz.

11. Coloration reactions:
    Positive to; ninhydrin, Greig-Leiback's and Lemieux reagents
    Negative to; Sakaguchi's and silver nitrate reagents 12. Nuclear magnetic resonance spectra:
    Hydrogen n.m.r. spectrum of SF-2052 substance-HCl in deutero-water (100 MHz, TMS external standard) is shown in FIG. 2 of the attached drawings. Main signals observed at 1.34 ppm(d), 2.00 ppm(m), 3.16 ppm(s), 3.51 ppm(s), 5.35 ppm(d) and 7.99 ppm(s). Carbon n.m.r. spectrum of SF-2052 substance-HCl in deutero-water (dioxane internal standard) is shown in FIG. 3.

13. Specific optical rotation:
    $[\alpha]_D^{25} = +87°$ (c 1, $H_2O$)

Taking into account of the above-mentioned physical and chemical properties of the SF-2052 substance hydrochloride, it is considered that SF-2052 substance free base is represented by the following structural formula:

Referring to the attached drawings.

Antibacterial activity of SF-2052 substance of this invention (as the sulfate) to inhibit the growth of various bacteria was estimated according to a standard serial dilution method using Heart Infusion agar as the incubation medium. The incubation was made at a temperature of 37° C. for 16 hours. The minimum inhibitory concentrations (mcg/ml) of the SF-2052 substance sulfate is listed in Table 1 below.

TABLE 1

| Antibacterial spectrum of SF-2052 substance (sulfate) | |
|---|---|
| Test microorganisms | MIC. (mcg/ml) |
| Bacillus subtillis PCI-219 | 1.56 |
| Staphylococcus aureus 209P | 3.12 |
| Sarcina lutea | 0.78 |
| Escherichia coli | 12.5 |
| Escherichia coli B | 6.25 |
| Escherichia coli K-12-R | 3.12 |
| Klebsiella pneumonia | 3.12 |
| Proteus vulgaris | 1.56 |

TABLE 1-continued

| Antibacterial spectrum of SF-2052 substance (sulfate) | |
|---|---|
| Test microorganisms | MIC. (mcg/ml) |
| Pseudomonas aeruginosa | 100 |
| Mycobacterium smegmatis 607 Km-R | 100 |
| Mycobacterium smegmatis 607 Sm-R | 1.56 |

From the results of the above table, it is clear that SF-2052 substance of this invention has a high antibacterial activity against both gram-negative and gram-positive bacteria.

SF-2052 substance having the chemical, physical and biological properties as described above is coincident with none of the known substances mentioned in the literature of the prior art, and it is evidently a new substance.

According to this invention, there is secondly provided a process of producing the SF-2052 substance, which comprises:

(a) cultivating an SF-2052 substance-producing strain of actinomycetes, especially a strain of Dactylosporangium matsuzakiense SF-2052 in an aqueous liquid culture medium containing assimilable carbon and nitrogen sources under aerobic conditions for a period of time sufficient to produce and accumulate the SF-2052 substance in the culture medium, and (b) recovering the SF-2052 substances from the culture.

The SF-2052 substance-producing microorganism, Dactylosporangium matsuzakiense SF-2052 strain employed according to this invention was isolated from a soil sample collected in Inagami-shrine at Matsuzaki-cho, Kamo-gun, Shizuoka-prefecture, Japan in February, 1977. Isolation of the SF-2052 strain was made by incubating an aqueous suspension of said soil sample on an isolating culture medium comprising 0.2% soluble starch, 0.04% ammonium sulfate, 0.02% di-potassium phosphate, 0.02% magnesium sulfate, 0.04% calcium carbonate and 1.5% agar (pH not adjusted) at 28° C. for 30 days. This SF-2052 strain has been deposited in a Japanese public depository "Fermentation Research Institute" at Chiba-city, Japan (now moved to Yatabe-cho, Tsukuba-gun, Ibaragi-prefecture, Japan) under deposit number FERM-P 4670, and also deposited in the American Type Culture Collection, Washington, D.C. U.S.A., under deposit number ATCC No. 31570 as of Sept. 26, 1979.

The SF-2052 strain has the following microbiological properties. The observations were made according to the method of E. B. Shirling and D. Gottlieb described in the "International Journal of Systematic Bacteriology" 16, 313–340 (1966).

I. Morphological observation:
Substrate mycelia are grown wavy with abundant branches and are of a diameter of 0.5 to 0.6 microns. On both the agar medium and on liquid media, no fragmentation of substrate mycelia is usually observed.

Aerial mycelia are not observed in almost cases and are considered not to be formed in fact. Substrate mycelium of the SF-2052 strain bears sporangia, singly or in tuft on the surface of agar medium. The sporangium is formed relatively abundantly on starch-agar medium but poorly on glycerol-asparagine agar, tyrosine agar and oatmeal agar media. Sporangium is of a finger-like shape and is of a size of 0.9–1.4 microns by 4.0–6.0 microns. Each sporangium usually contains a single row of three spores. Almost of the spore is of a cylindrical or oval shape, and the surface structure of spore is smooth. Each spore has a size of 0.8–1.3 microns by 1.1–1.6 microns. When the spores are suspended in an aqueous extract of soil, for example, and allowed to stand for 15–30 minutes, they exhibit motile.

II. Cultural characteristics on different culture media:

The cultural characteristics of the SF-2052 strain are shown in Table 2 below. In the following table, the descriptions of colors given in a bracket [ ] are based on the standard of Color Harmony Manual of Container Corporation of America. The incubation was made at 28° C. and the observation was done after incubation for 21 days.

TABLE 2

| Culture medium | Growth and Color | Aerial mycelium | Soluble pigment |
|---|---|---|---|
| Sucrose-nitrate agar | Ordinary growth, amber to faintly orange (3 lc) | None | None |
| Glucose-asparagine agar | Ordinary growth, reddish orange (4 pc) | None | None |
| Glycerol-asparagine agar | Faint thin growth, faintly mellon-yellow (3 ea) | None | None |
| Starch agar | Ordinary to good growth, reddish orange (4 pc) | None | None |
| Oatmeal agar | Ordinary growth, orange (4 lc-5 nc) | None | None |
| Yeast extract-malt extract agar | Ordinary growth, wrinkled, amber to light brown (3 lc-4 ng) | None | None |
| Tyrosine agar | Good growth, faintly grayish orange to light brown (4 lc-4 ng) | None | Brownish pink |
| Nutrient agar | Very faint growth, faintly orange | None | None |
| Bennet agar | Ordinary to good growth, reddish orange (4 pc-5 pc) | None | None |
| Calcium malate agar | Faint to ordinary growth, light orange (3 ga-4 ga) | None | None |

III. Physiological properties:
(1) Growth temperature range: The SF-2052 strain grows in a temperature range of 15°–40° C. on starch-agar medium. The optimum growth temperature is in a range of 25°–37° C.
(2) Liquefaction of gelatine: No liquefaction occurs when incubated at 20° C. for 21 days.
(3) Hydrolysis of starch: Positive (when incubated at 28° C. for 21 days)
(4) Reduction of nitrate: Negative (when incubated at 28° C. for 21 days)
(5) Coagulation of skimmed milk: Negative (when incubated at 28° C. for 21 days)
(6) Peptonization of skimmed milk: Negative (when incubated at 28° C. for 21 days)
(7) Formation of melanoid pigment: Negative IV. Utilization of carbon sources: Estimation was made with incubating at 28° C. in an incubation medium of the composition comprising:

| Yeast extract (Difco) | 5 g. |
| Calcium carbonate | 1 g. |
| Agar (Difco) | 15 g. |
| Distilled water | 1000 ml |

The results of estimation is tabulated in Table 3 below.

TABLE 3

| Carbon source | Growth |
|---|---|
| D-glucose | +++ |
| D-xylose | +++ |
| D-fructose | ++ |
| L-arabinose | +++ |
| D-mannitol | +++ |
| I-inositol | + |
| Rhamnose | +++ |
| Sucrose | +++ |
| Raffinose | + |
| No addition | + |

V. Chemical composition of cell wall:

The chemical composition of cell wall and whole cell of the SF-2052 strain was analyzed according to the method of T. Yamaguchi described in the "J. Bact." 89, 444–453 (1965); according to the method of B. Becker et al described in the "Appl. Microbiol." 12, 421–423 (1964); or according to the method of M. P. Lechevalier described in the "J. Lab. Clin. Med." 71, 934–944 (1968).

From the analytical results so obtained, it is found that the SF-2052 strain belongs to cellular wall type-II as its cellular wall contains hydroxydiamino-pimellic acid and glycine. Furthermore, its whole cell sugar pattern is belonging to A- or D-type, as the hydrolysate of the whole cell is observed to contain xylose and galactose together with a trace of arabinose.

In view of the above-mentioned properties of the SF-2052 strain, it is considered that the SF-2052 strain is a strain belonging to the genus Dactylosporangium among the order Actinomycetales. Of the species of the genus Dactylosporangium, two species, *Dactylosporangium aurantiacum* and *Dactylosporangium thailandense* are already known (J. E. Thiemann et al, "Arch. Mikrobiol." 58, 42–52 (1967) and "Bergey's Manual of Determinative Bacteriology" 8th Ed., 1974). A comparison of the SF-2052 strain with these known species is summarized in Table 4 below.

TABLE 4

| Properties | SF-2052 strain | D. aurantiacum | D. thailandense |
|---|---|---|---|
| Growth on glucose-asparagine-agar medium | Ordinary growth, reddish orange | Ordinary growth, white | Ordinary growth, faintly orange |
| Formation of sporangium on calcium malate-agar medium | None | Abundant | Abundant |
| Growth on nutrient agar medium | Very faint growth, light orange | Very good growth, white | Good growth, orange |
| Production of soluble pigment on Hickey and | None | None | Reddish brown |

TABLE 4-continued

| Properties | SF-2052 strain | D. aurantiacum | D. thailandense |
|---|---|---|---|
| Tresner-agar medium | | | |
| Growth on potato plug | No growth | Very faint growth, lightly orange | Very faint growth, reddish brown |
| Liquefaction of gelatine | Negative | Negative | Positive |
| Reduction of nitrate | Negative | Positive | Negative |
| Peptonization of skimmed milk | Negative | Positive | Positive |
| Utilization of raffinose | Not utilized[*3] | Utilized[*1] | Well utilized[*2] |

Notes:
[*1] On the incubation medium described by J.E. Thiemenn in the "Arch. Mikrobiol." 58, 42–52 (1967).
[*2] On an incubation medium specified in the above note [*1] but further containing amounts of vitamins.
[*3] On yeast extract-calcium carbonate-agar medium. The SF-2052 strain did not grow on the media [*1] and [*2].

The SF-2052 strain is not coincident with either of the known species of the genus Dactylosporangium and hence the SF-2052 strain is properly deemed as a new species and designated as *Dactylosporangium matsuzakiense* SF-2052.

It is further now found that the SF-2052 substance is also produced by a new microorganism designated Micromonospora sp. SF-2098 (identified as FERM-P 5073 or ATCC No. 31580).

In carrying out the fermentative production of the SF-2052 substance according this invention, using *Dactylosporangium matsuzakiense* SF-2052 strain, the SF-2052 substance-producing strain for present use may be cultivated in a manner known per se in a culture medium containing nutrient sources which are assimilable by ordinary microorganisms. For this purpose, use may be made of any known nutrients which have been employed generally for the cultivation of known strains of the *actinomycetes*. Example of the nutrient sources include glucose, glycerine, sucrose, starch, dextrin, maltose syrup, molasses and soybean oil as the carbon source; and soybean meal, wheat embryo, meat extract, peptone, yeast extract, dried yeast, corn steep liquor, cotton seed meal, ammonium sulfate and sodium nitrate as the nitrogen source. If required, inorganic salts such as calcium carbonate, sodium chloride, potassium chloride, cobalt chloride, phosphates and the like may be added. In addition, such organic or inorganic materials as ones useful to aid the growth of the SF-2052 strain employed and to promote the production of the SF-2052 substance may be incorporated in the culture medium.

As the cultivation procedures which can be adopted in this invention, liquid cultivation and particularly liquid cultivation under submerged conditions is most preferred in general, as the case be in the production of known antibiotics. In the present process, the cultivation is conducted under aerobic conditions. The SF-2052 strain may suitably be incubated at a temperature of 25°–37° C. and most frequently at a temperature of 28°–32° C. In this situation, the production of the SF-2052 substance in the culture broth reaches a maximum at the end of 2 to 10 days of incubation, either in shake-cultivation method or in tank-cultivation method. The SF-2098 strain may suitably be incubated at a temperature of 25°–40° C. and normally at a temperature in the vicinity of 30° C. The incubation medium is preferably maintained at a neutral or weakly alkaline pH value.

For assay of the SF-2052 substance produced by this invention, the following procedure may be used: the assaying culture medium comprising 0.5% polypeptone, 0.3% beef extract and 1.5% agar (pH 7.0) is employed, and *Bacillus subtillis* PCI-219 is employed as the assaying microorganism. In this assaying method, at a concentration of 50 mcg/ml to 10 mcg/ml of the SF-2052 substance, the relation between the logarithm of the concentration and the diameter of the inhibition zone can be plotted linearly, giving the inhibition zone of 21.2 to 12.8 mm as determined by the conventional paper-disc plate method.

The SF-2052 substance of this invention is a water-soluble basic antibiotic, and the SF-2052 substance as produced by the cultivation of the SF-2052 strain is mainly present in the liquid phase of the culture broth and may be recovered from the culture by utilizing the physico-chemical properties of the SF-2052 substance. Recovery and purification of the SF-2052 substance may be performed by a chromatographic procedure using a synthetic adsorbent resin such as Amberlite XAD-2 (a synthetic adsorbent resin consisting of a microporous copolymer of styrene and divinylbenzene, a product of Rohm & Haas Co., U.S.A.) and Diaion HP-20 (a synthetic adsorbent resin consisting of a microporous copolymer of styrene and divinylbenzene, a product of Mitsubishi Kasei Co., Japan) or a gel-filtration agent such as Sephadex G-10 (a gel-filtration agent consisting of dextran cross-linked by epichlorohydrin, a product of Pharmacia Co., Sweden) and Sephadex LH-20 (a gel consisting of a derivative of dextran sulfate, a product of Pharmacia Co., Sweden); or a cation-exchange resin such as Amberlite IRC-50 or Amberlite CG-50 (a weakly acidic cation-exchange resin consisting of a copolymer of methacrylic acid and divinylbenzene, a product of Rohm & Haas Co., U.S.A.) and CM-Sephadex (a gel-filtration agent made of a carboxymethyl-substituted cross-linked dextran gel, a product of Pharmacia Co., Sweden). The following procedure is efficient to recover the SF-2052 substance from the culture broth. Thus, the culture broth containing the SF-2052 substance is freed from the solid contents by filtration or centrifugation, and the resulting broth filtrate is treated with Diaion HP-20 resin (a synthetic adsorbent resin, a product of Mitsubishi Kasei Co., Japan) for adsorption of the active substance, and then the active substance is eluted from the resin by developing with 50% aqueous acetone (water-acetone mixture, 1:1 by volume) (pH, not adjusted) and 50% aqueous acetone (pH 2.0 adjusted by hydrochloric acid) as the eluent, and the eluate obtained is concentrated under reduced pressure to obtain a crude powdery product of the SF-2052 substance hydrochloride.

This crude product is then purified by a column-chromatography using CM-Sephadex (H+ form), CM-Sephadex (Na+ form) and/or active carbon in a proper combination so as to yield a highly purified product of the SF-2052 substance hydrochloride. As the SF-2052 substance free base is very instable under alkaline conditions, it is difficult to obtain a pure product of this substance as the free base form. It is important to carry out the recovery and purification of the SF-2052 substance always under neutral or acidic conditions, and it is recommendable that a weakly acidic aqueous solution of the SF-2052 substance is freeze-dried at a final stage of recovery and isolation to give the SF-2052 substance as its hydrochloride or sulfate in the form of a colorless, amorphous powder.

For determination of acute toxicity of the SF-2052 substance sulfate, this was intravenously injected as its solution in isotonic aqueous solution of sodium chloride into several groups of mice. It is estimated that the SF-2052 substance sulfate shows an $LD_{50}$ value of 350 mg/kg upon intravenous injection in mice and is substantially non-toxic. According to this invention, therefore, there is further provided an antibacterial composition comprising as the active ingredient an antibacterially effective amount of at least one of the pharmaceutically acceptable acid-addition salts of the SF-2052 substance, in association with a pharmaceutically acceptable liquid or solid carrier. The content of this active ingredient in this antibacterial composition may be in a range of 5% to 50% by weight of the composition.

The antibacterial composition of this invention may be formulated into an aqueous solution containing 0.01% to 0.1% by weight of the SF-2052 substance acid-addition salt which is useful for sterilization of surgical material and instruments as well as another devices and places which are desirably kept sterile. Moreover, the antibacterial composition of this invention may be formulated as conventional orally administrable forms such as tablets, capsules, powders, solutions and suspensions, either by admixing an amount of a pharmaceutically acceptable acid-addition salt of the SF-2052 substance of this invention with a conventional pharmaceutically acceptable solid carrier such as starch, sucrose, talc and calcium carbonate or by dissolving or suspending it in a pharmaceutically acceptable liquid carrier such as ethanol and water. The proportion of the active substance of this invention to the solid or liquid carrier may be chosen appropriately depending on the form of the orally administerable formulation prepared and usually may be in a ratio of from 1:1 to 1:100 by weight.

The antibacterial composition of this invention may also be formulated into injectable solutions or suspensions by dissolving or suspending the active substance at a suitable level of from 0.1% to 10% by weight into a physiological saline solution or other conventional pharmaceutically acceptable liquid vehicle such as Ringer's solution, with or without aid of a suitable dispersion agent. The injectable solution or suspension so prepared may be given, eg. by intravenous injection, intramuscular injection or intraperitoneal injection.

It will be appreciated that the actual preferred dosage of the active substance of this invention used will vary according to the particular composition formulated for administration, the mode of administration and the particular disease to be treated. Many factors that modify the action of the drug of this invention will be taken into account by the skilled in the art, for example, age, body weight, sex, diet, time of administration, route of administration, rate of excretion, drug combinations, reaction sensitivities and severity of the disease. Generally, about 0.5 mg/kg to about 100 mg/kg of the active compound is given a day to an adult person. Optimal dosages for a given set of conditions of a patient can be ascertained by the skilled in the art using conventional dosage determination tests in view of the above guidelines and in view of the past experiences as obtained when determining suitable dosages of the previously known antibacterial agent.

The invention is now illustrated with reference to the following Examples to which the invention is limited in no way.

EXAMPLE 1

(1) Incubation of the SF-2052 strain

A stock culture of *Dactylosporangium matsuzakiense* SF-2052 (identified as FERM-P 4670 or ATCC No. 31570) was used, and a sterilized seed culture medium comprising 2.0% glucose, 0.5% peptone, 0.2% meat extract, 0.3% yeast extract, 0.2% soybean meal and 0.1% calcium carbonate (pH 7.0 before the sterilization) was employed for the incubation.

5 to 6 loopful amounts of the above-mentioned stock culture were inoculated to 20 ml of the aforesaid seed culture medium in a 100 ml-Erlenmeyer flask, followed by incubation at 28° C. for 6 days to give a first seed culture. Production of this first seed culture was made in 10 flasks. Totally 200 ml of the first seed culture was inoculated in 20 ml-portions to 10 Erlenmeyer flasks of 500 ml-capacity each containing 80 ml of the aforesaid seed culture medium, followed by incubation at 28° C. for 72 hours.

In this way, the second seed culture was obtained, and this was further inoculated in 5 ml-portions to 150 Erlenmeyer flask of 500 ml-capacity each containing 80 ml of a production culture medium. The production culture medium employed had such a composition comprising 4.0% glucose, 1.0% peptone, 0.4% meat extract, 0.6% yeast extract, 0.4% soybean meal and 0.2% calcium carbonate, namely containing the nutrient component each in two-fold quantity than that of the respective nutrient components present in the aforesaid seed culture medium. The cultivation was made at 28° C. for 6 days according to a conventional shake-cultivation method.

After the cultivation, the culture broth was subjected to a continuous centrifugation using a freezer-centrifugator (manufactured by Tommy Company, Japan), giving 10 liters of the broth filtrate in about 2 hours of the centrifugation operation.

(2) Recovery of the SF-2052 substance

The broth filtrate (10 liters) obtained in the above was passed through a column of 750 ml of Diaion HP-20 (a synthetic adsorbent resin, a product of Mitsubishi Kasei Co., Japan) for adsorption of the active substance. The resin column was washed with 3 l of water, followed by elution with 1.8 l of 50% aqueous acetone (pH, not adjusted) and then with 1.8 l of 50% aqueous acetone (pH 2.0, adjusted by HCl). In this way, the SF-2052 substance was eluted out from the resin column. The eluate was collected in 1.8 l-fractions.

The active fractions (totally 3.6 l) containing the SF-2052 substance was concentrated under reduced pressure to a smaller volume by distilling off the acetone. The resulting concentrate was allowed to stand and then filtered to remove the precipitate deposited. The filtrate was passed through a column of 300 ml of CM-Sephadex C-25 (H+ form) (a gel-filtration agent, a product of Pharmacia Co., Sweden) for adsorption of the active substance.

The CM-Sephadex column was washed with 1.0 l of 0.1 M aqueous sodium chloride, with 1.0 l of 0.2 M aqueous sodium chloride and then with 3 l of 0.4 M aqueous sodium chloride, followed by elution with 0.6 M aqueous sodium chloride. The eluate was collected in 18 ml-fractions, and the active substance was eluted out in the fractions Nos. 26 to 92.

The active fractions were passed through a column of 200 ml of chromatographic active carbon (a product of Wako Junyaku Co., Japan) for adsorption of the active substance, and the carbon column was washed with 900 ml of water, followed by elution with 1.2 l of 50% aqueous acetone (pH, not adjusted) and then with 600 ml of 50% aqueous acetone (pH 2.0, adjusted by HCl). The eluate was collected in 1800 ml-fractions, and the active fraction (totally 1800 ml) containing the SF-2052 substance eluted out (totally 1.8 l) were combined together and the combined solution was concentrated under reduced pressure. The concentrated solution was freeze-dried to give 170 mg of a crude, white-colored powdery product (purity, ca. 20%) of the SF-2052 substance hydrochloride.

(3) Purification

The crude product powder (170 mg) of the SF-2052 substance (HCl) obtained in the above procedure (2) of Example 1 was taken up into 5 ml of water, and the resulting aqueous solution was passed through a column of 180 ml of CM-Sephadex C-25 (Na+-form) which had been impregnated with 0.1 M aqueous sodium chloride. This CM-Sephadex column was eluted with 2 l of 0.5 M aqueous sodium chloride, followed by development with 1.0 M aqueous sodium chloride. The effluent was collected in 18 ml-fractions, and the active fractions Nos. 8 to 20 containing the SF-2052 substance eluted out were combined together.

The active fractions (totally 220 ml) was passed through a column of 40 ml of chromatographic active carbon for adsorption of the active substance. The carbon column was washed with 250 ml of water, followed by elution with 200 ml of 50% aqueous acetone (pH, not adjusted) and then with 200 ml of 50% aqueous acetone (pH 2.0) to elute the active substance out of the column. The eluate was collected in 400 ml-fractions, and the active fraction (totally 400 ml) was concentrated under reduced pressure. The concentrated solution was freeze-dried to give 26 mg of the SF-2052 substance hydrochloride as a colorless powder which is pure.

(4) Formation of SF-2052 substance sulfate

The colorless powder (26 mg) of the pure SF-2052 substance hydrochloride obtained in the above procedure (3) was taken up into 10 ml of water, and the solution obtained was passed through a column of 10 ml of a strongly basic anion-exchange resin, Amberlite IRA-400 (sulfate form) (a product of Rohm & Haas Co., U.S.A.). The effluent running out of the resin column was concentrated and freeze-dried to give 30 mg of the SF-2052 substance sulfate as a colorless powder. This product showed a decomposition point above 220° C.

EXAMPLE 2

The broth filtrate (10 l) obtained from the cultivation procedure of Example 1 (1) was passed through a column of 800 ml of a synthetic adsorbent resin, Diaion HP-20 (a product of Mitsubishi Kasei Co., Japan) for adsorption of the active substance. The resin column was washed with 4 l of water and then eluted with 50% aqueous acetone (pH 4.0) while the eluate was collected in 500 ml-fractions. The fractions Nos. 2 to 6 contained the active substance eluted out, and these active fractions were combined together and concentrated under reduced pressure by distilling off the acetone.

The concentrated solution was left to stand and then filtered to remove the precipitate deposited. The filtrate was passed through a column of 250 ml of an cation-exchange resin, Amberlite IRC-50 (Na+ form) (a product of Rohm & Haas Co., U.S.A.) for adsorption of the active substance. The resin column was subsequently washed with 2 l of water and eluted with 0.1 N hydrochloric acid. The eluate was collected in 18 ml-fractions, and the active substance was eluted out in the fraction Nos. 240 to 336. These active fractions were combined together and passed through a column of 150 ml of an anion-exchange resin, Amberlite IR-45 (OH− form) for neutralization.

The solution (pH 5.4) coming out of the column was placed into a column of 80 ml of chromatographic active carbon for adsorption of the active substance, and the carbon column was washed with 400 ml of water and then eluted with 300 ml of 50% aqueous acetone (pH, not adjusted) and then with 300 ml of 50% aqueous acetone (pH 2.4, adjusted by HCl) to desorb the active substance from the resin column.

The combined active solution so obtained (totally 600 ml) was concentrated under reduced pressure and freeze-dried to give 260 mg of the SF-2052 substance hydrochloride as a faintly yellow colored crude powder (purity 16%).

What we claim is:

1. A substance, SF-2052 substance or a pharmaceutically acceptable acid addition salt thereof; the SF-2052 substance being a water-soluble basic compound having antibacterial activity, and the SF-2052 substance hydrochloride being in the form of a colorless and amorphous powder which is substantially stable under neutral to acidic pH conditions but instable under alkaline pH conditions, which shows no definite melting point but discolors into brown gradually at or near 170° C. and is decomposed at 209°-210° C. with foaming, which shows positive reaction with ninhydrin, Lemieux reagent and Greig-Leiback's reagent but negative reaction with Sakaguchi's reagent and silver nitrate and which is readily soluble in water, soluble in methanol and insoluble in ethyl acetate, chloroform, benzene and ethylether;

the SF-2052 substance hydrochloride being further characterized by:
(a) exhibiting an elemental analysis: C 35.69%, H 7.04%, N 11.80%,
(b) having no characteristic absorption peak at 220 nm to 370 nm in ultraviolet absorption spectrum in aqueous solution,
(c) having an infrared absorption spectrum in potassium bromide pellet corresponding to that shown in FIG. 1 of the attached drawings,
(d) having a hydrogen nuclear magnetic resonance absorption spectrum in deutero-water substantially corresponding to that shown in FIG. 2 of the attached drawings,
(e) having a carbon nuclear magnetic resonance absorption spectrum in deutero-water substantially corresponding to that shown in FIG. 3 of the attached drawings, (f) having a specific optical rotation $[\alpha]_D^{25} = +87°$ (c=1, water) in aqueous solution, and (g) giving a single spot as Rf=0.46 in a cellulose thin layer chromatography with n-propanol-pyridine-acetic acid-water (15:10:3:12) as the developing solvent and at Rf=0.09 in a paper chromatography with n-butanolacetic acid-water (2:1:1) as the developing solvent according to the ascending method.

2. The substance of claim 1 which is the SF-2052 substance hydrochloride or sulfate.

3. A process of producing the SF-2052 substance of claim 1, which comprises:

(a) cultivating an SF-2052 substance-producing strain of actinomycetes, especially a strain of *Dactylosporangium matsuzakiense* SF-2052 identified as FERM-P 4670 or ATCC number 31570 in an aqueous liquid culture medium containing assimilable carbon and nitrogen sources under aerobic conditions for a period of time sufficient to produce and accumulate the SF-2052 substance in the culture medium, and (b) recovering the SF-2052 substance from the culture.

4. A process of claim 3 in which the cultivation is conducted at a temperature of 25°–37° C. for a time of 2 to 10 days.

5. A process of claim 3 in which the SF-2052 substance is recovered as its hydrochloride from the culture broth of *Dactylosporangium matsuzakiense* SF-2052.

6. An antibacterial composition comprising as the active ingredient an antibacterially effective amount of a pharmaceutically acceptable acid-addition salt of the SF-2052 substance of claim 1, in association with a pharmaceutically acceptable carrier for the active ingredient.

* * * * *